United States Patent
Chiou et al.

(10) Patent No.: US 11,730,548 B2
(45) Date of Patent: Aug. 22, 2023

(54) OPTICAL COHERENCE TOMOGRAPHY SCANNING PROBE

(71) Applicant: INDUSTRIAL TECHNOLOGY RESEARCH INSTITUTE, Hsinchu (TW)

(72) Inventors: De Yi Chiou, New Taipei (TW); Kai-Hsiang Chen, Hsinchu (TW); Chi Shen Chang, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 139 days.

(21) Appl. No.: 17/125,785

(22) Filed: Dec. 17, 2020

(65) Prior Publication Data
US 2022/0192750 A1 Jun. 23, 2022

(51) Int. Cl.
*A61B 34/20* (2016.01)
*G02B 26/10* (2006.01)
(Continued)

(52) U.S. Cl.
CPC ........... *A61B 34/20* (2016.02); *A61B 5/0066* (2013.01); *A61N 1/0534* (2013.01);
(Continued)

(58) Field of Classification Search
CPC ..... A61B 34/20; A61B 5/0066; A61B 5/0042; A61B 2034/2055; A61B 2090/306;
(Continued)

(56) References Cited

U.S. PATENT DOCUMENTS

| 4,280,512 A | 7/1981 | Karr et al. |
| 6,445,939 B1 | 9/2002 | Swanson et al. |

(Continued)

FOREIGN PATENT DOCUMENTS

| CN | 102894947 B | 4/2015 |
| CN | 104955372 B | 2/2017 |

(Continued)

OTHER PUBLICATIONS

Extended European Search Report from Corresponding EP Application No. 21215065.0, dated May 4, 2022.
(Continued)

*Primary Examiner* — Joel Lamprecht
(74) *Attorney, Agent, or Firm* — Maschoff Brennan (57) ABSTRACT

An OCT scanning probe includes a tubular housing, at least one electrode, an optical fiber scanner and an auxiliary localization component. The electrode is disposed on an outer surface of the tubular housing. The optical fiber scanner is disposed in the tubular housing and includes an optical fiber and an optical element. The optical element is disposed on an emitting end of the optical fiber and at corresponding position to a light transmittable portion of the tubular housing. The auxiliary localization component is disposed on the tubular housing, and overlaps part of the light transmittable portion. A light beam emitted from the optical fiber scanner passes through the light transmittable portion to obtain a tomographic image. An interaction of the light beam with the auxiliary localization component causes a characteristic in the tomographic image, with the characteristic corresponding to the auxiliary localization component.

13 Claims, 10 Drawing Sheets

(51) Int. Cl.
*G02B 27/10* (2006.01)
*A61N 1/05* (2006.01)
*A61B 5/00* (2006.01)

(52) U.S. Cl.
CPC ......... *G02B 26/103* (2013.01); *G02B 27/106* (2013.01); *A61B 5/0042* (2013.01); *A61B 2034/2055* (2016.02)

(58) Field of Classification Search
CPC ......... A61B 2090/3735; A61N 1/0534; G02B 26/103; G02B 27/106; G02B 23/26; G02B 26/108; G02B 23/2423
See application file for complete search history.

(56) References Cited

U.S. PATENT DOCUMENTS

| | | | |
|---|---|---|---|
| 9,574,870 | B2 | 2/2017 | Yamazaki et al. |
| 10,362,942 | B2 | 7/2019 | Mak et al. |
| 10,463,254 | B2 * | 11/2019 | Tearney ............... A61B 5/0066 |
| 10,568,687 | B2 | 2/2020 | Chen et al. |
| 2004/0162487 | A1 | 8/2004 | Klingenbeck-Regn et al. |
| 2005/0187422 | A1 | 8/2005 | Maschke |
| 2006/0142830 | A1 | 6/2006 | Maschke |
| 2010/0123903 | A1 | 5/2010 | Lu et al. |
| 2012/0184971 | A1 | 7/2012 | Zentgraf et al. |
| 2015/0173619 | A1 | 6/2015 | Zvuloni et al. |
| 2015/0320318 | A1 | 11/2015 | Yamazaki et al. |
| 2019/0008389 | A1 | 1/2019 | Mak et al. |
| 2019/0200851 | A1 | 7/2019 | Chen et al. |
| 2019/0293414 | A1 | 9/2019 | Sorimoto |
| 2019/0374196 | A1 | 12/2019 | Courtney et al. |
| 2019/0391338 | A1 | 12/2019 | Tearney et al. |

FOREIGN PATENT DOCUMENTS

| | | |
|---|---|---|
| CN | 109152548 A | 1/2019 |
| CN | 109843201 A | 6/2019 |
| DE | 2843096 A1 | 4/1980 |
| DE | 3300050 A1 | 7/1984 |
| DE | 10255957 A1 | 8/2004 |
| JP | H1156786 A | 3/1999 |
| JP | 2005-230552 A | 9/2005 |
| JP | 2015-514494 A | 5/2015 |
| TW | 201019884 A | 6/2010 |

OTHER PUBLICATIONS

Ahsen et al., "Correction of rotational distortion for catheter-based en face OCT and OCT angiography," Optics Letters, vol. 39, No. 20, Oct. 15, 2014, pp. 5973-5976.

Krapohl et al., A New Integrated Optical and Electrophysiological Sensor, Biomed. Technik/Biomedical Engineering. (2008) vol. 53. 126-128.

TW Office Action in Application No. 109144597 dated Mar. 25, 2022.

Japanese Office Action dated Mar. 14, 2023 as received in application No. 2021-204302.

* cited by examiner

OPTICAL COHERENCE TOMOGRAPHY SCANNING PROBE

BACKGROUND

1. Technical Field

This present disclosure relates to an optical coherence tomography (OCT) scanning probe.

2. Related Art

With the development of medical technology, the treatment of Parkinson's disease has evolved from the administration of levodopa at the beginning of course to the regulation of brain activities by surgery at the middle or late stage of course to compensate for the limitations and side effects of medication. At present, deep brain stimulation (DBS) is a primary surgery for Parkinson's disease. DBS involves the implantation of a thin lead with electrode in specific target such as subthalamic nucleus (STN) or internal globus pallidus, and the placement of a medical device which sends electrical current to effect the physiology of brain cells and neurotransmitters, such that dyskinesia can be well controlled and movement of patient's limbs can be improved.

DBS generally includes the following procedures: (1) DBS target localization procedure; and (2) DBS electrode implantation procedure. During the DBS target localization procedure, a magnetic resonance imaging (MRI) of patient's head is firstly performed for surgical path planning; then, a microelectrode recording (MER) probe is inserted into patient's head along the predetermined surgical path for detecting physiological signals of brain cells to determine the location of surgical target. During the DBS electrode implantation procedure, a permanent DBS lead is implanted according the location of surgical target.

The conventional DBS suffers some problems related to inaccurate localization in the target localization procedure. Although MRI and MER help to confirm the location of surgical target. It is difficult for surgeons to identify surgical target (STN or internal globus pallidus) from MRI images due to small size of the surgical target. Also, inevitable brain shift caused by cerebrospinal fluid leakage and intracranial pressure may change the location of surgical target. Moreover, MER merely provides one dimensional spatial information (for example, information along an insertion direction of the microelectrode). The lack of three dimensional spatial information results in a problem that the surgeon cannot check a position of the electrode with respect to the surgical target and whether the electrode tip is at expected lactation, even though the electrode tip can be traced according to the electrophysiological recording of brain cells, and thus the surgeon lacks sufficient information as reference for subsequent adjustment of surgical path.

SUMMARY

In view of the above problems, it is necessary to improve the brain positioning method of DBS. The present disclosure provides an optical coherent tomography probe suitable for DBS, which helps to solve the problem that the target cannot be accurately positioned before the surgery or the electrode position cannot be accurately located during the surgery.

According to one aspect of the present disclosure, an OCT scanning probe includes a tubular housing, at least one electrode, an optical fiber scanner and an auxiliary localization component. The electrode is disposed on an outer surface of the tubular housing. The optical fiber scanner is disposed in the tubular housing. The optical fiber scanner includes an optical fiber and an optical element. The optical element is disposed on an emitting end of the optical fiber, and the optical element is at corresponding position to a light transmittable portion of the tubular housing. The auxiliary localization component is disposed on the tubular housing, and the auxiliary localization component overlaps part of the light transmittable portion. A light beam emitted from the optical fiber scanner passes through the light transmittable portion to obtain a tomographic image. An interaction of part of the light beam with the auxiliary localization component causes a characteristic in the tomographic image, with the characteristic corresponding to the auxiliary localization component.

The above description based on the content of the disclosure and description of the following exemplary embodiment and the embodiment to explain the principles and spirit of the present disclosure, and the scope of the patent application to provide further explanation of the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

According to the present disclosure, an auxiliary localization component overlaps a light transmittable portion of a tubular housing, such that a light beam emitted from an optical fiber scanner is blocked or reflected by the auxiliary localization component when passing through the light transmittable portion, thereby causing a characteristic (dark zone or bright zone) in a tomographic image. The location of the OCT scanning probe with respect to a surgical target can be determined according to the characteristic. Thus, the OCT scanning probe helps to position the target or determine whether the electrode is at the central region of the target. Once there is an offset between the electrode and the central region of the target, a surgeon can adjust a DBS lead implantation path according to the tomographic image, which is helpful to improve the therapeutic effect of DBS.

According to one embodiment of the present disclosure, an OCT scanning probe includes tubular housing, electrode, optical fiber scanner and auxiliary localization component. Please refer to FIG. 1 which is a schematic view of an OCT scanning probe according to a first embodiment of the present disclosure. In this embodiment, the OCT scanning probe 1a includes a tubular housing 10, an electrode 20, an optical fiber scanner 30 and an auxiliary localization component 40.

Figure 1:
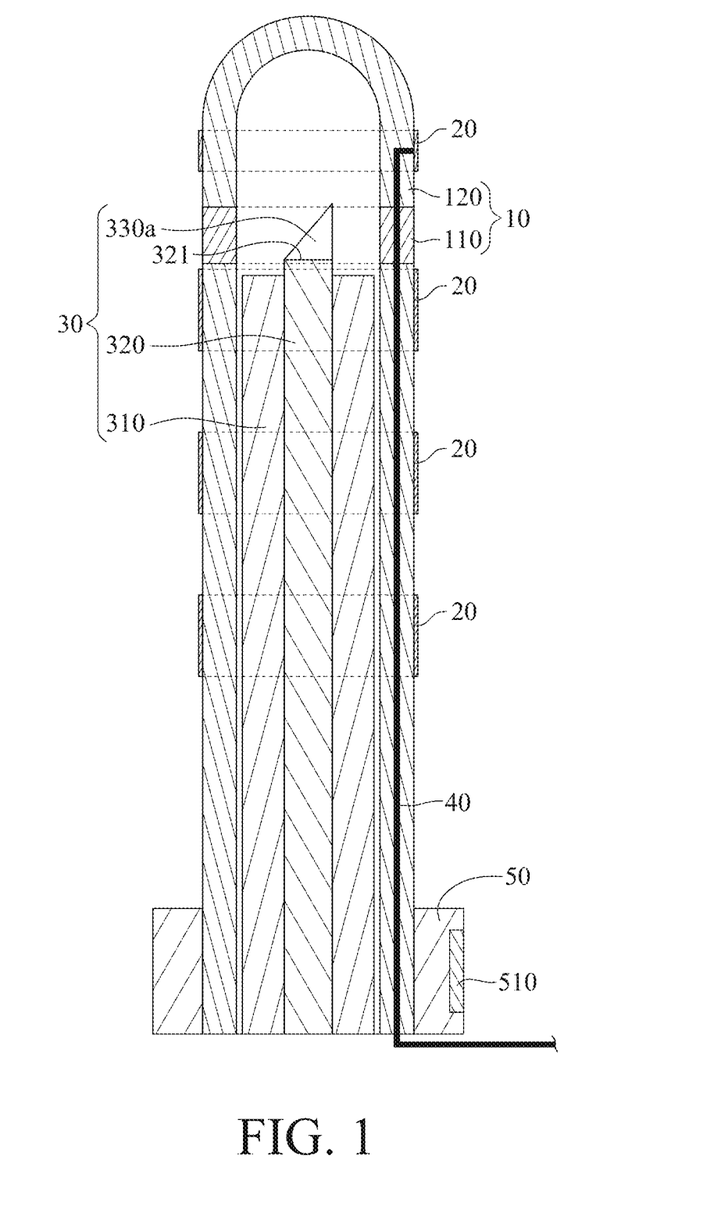
FIG. 1 is a schematic view of an OCT scanning probe according to a first embodiment of the present disclosure.

The tubular housing 10, for example, is a glass tube including a light transmittable portion 110 and an opaque portion 120, but the present disclosure is not limited thereto; in some embodiments, the tubular housing 10 may be made of light transmittable material such as glass, such that every portion of the tubular housing 10 is light transmittable. In this embodiment, the light transmittable portion 110 is located on a side wall of the tubular housing 10, but the present disclosure is not limited to specific location of the light transmittable portion 110.

The electrode 20, for example, is an electrode ring disposed on an outer surface of the tubular housing 10. The tubular housing 10 and the electrode 20 jointly constitute a DBS electrode. The electrode 20 can be electrically connected with external power supply (not shown in the drawings) for activating tissues, such as brain tissue, outside the OCT scanning probe 1a. In FIG. 1, there are multiple electrodes 20 on the tubular housing 10, but the present disclosure is not limited to the number of electrode 20; in some embodiments, single electrode 20 may be provided for measurement. The electrode 20 can be turned on to activate brain tissues or measure electrophysiological recordings of brain cells.

The optical fiber scanner 30 is disposed in the tubular housing 10, and the optical fiber scanner 30 includes a base 310, an optical fiber 320 and an optical element 330a. The optical fiber 320 is disposed on the base 310, and the optical element 330a is at corresponding position to the light transmittable portion 110 of the tubular housing 10. In one embodiment, the base 310 is rotatably disposed in the tubular housing 10. Thus, the base 310 brings the optical fiber 320 to together rotate about a central axis of the base 310 with respect to the tubular housing 10; in some embodiments, the optical fiber 320 rotatably disposed in the base 310, and the optical fiber 320 can be used for scanning due to its rotation with respect to the base 310. In this embodiment, the optical fiber 320 further includes an emitting end 321 of the optical fiber 320, and the optical element 330a is disposed on the emitting end 321. Since the light transmittable portion 110 is located on the side wall of the tubular housing 10, the optical element 330a in this embodiment may be a reflector for changing a traveling direction of light beam emitted from the optical fiber 320. Said light beam from the optical fiber 320 can be reflected by the optical element 330a, and then travels through the light transmittable portion 110 to the outside of the OCT scanning probe 1a. Therefore, the light beam reaches tissues outside the OCT scanning probe 1a, and the light beam is reflected by the tissues so as to be received by image sensor (not shown in the drawings) connected to the end of the optical fiber 320, and thus the image sensor generates one or more tomographic images. The present disclosure is not limited to the reflector working with the optical element 330a in this embodiment; in some embodiments, suitable optical component can be selected as the optical element 330a according to the location of the light transmittable portion, and the present disclosure is not limited to example(s) mentioned above.

Moreover, in this embodiment, the optical fiber scanner 30 is detachably sleeved in the tubular housing 10 so as to be removable from the tubular housing 10, and the optical fiber scanner 30 is movable along the central axis of the tubular housing 10, but the present disclosure is not limited thereto; in some embodiments, the optical fiber scanner 30 may be fixed inside the tubular housing 10.

In this embodiment and some other embodiments, said "light transmittable portion" of the tubular housing refers to a portion which is transmittable to the light beam emitted from the optical fiber. For example, as the light beam emitted from the optical fiber is visible light, the light transmittable portion is transmittable to light having visible wavelengths; as the light beam emitted from the optical fiber is infrared light, the light transmittable portion is transmittable to light having infrared wavelengths.

The auxiliary localization component 40 is disposed on the tubular housing 10, and the auxiliary localization component 40 overlaps part of the light transmittable portion 110. In this embodiment, the auxiliary localization component 40, for example, is a conductive line inside the side wall of the tubular housing 10, and the conductive line is electrically connected with the electrodes 20. The auxiliary localization component 40 can be electrically connected with external power supply (now shown in the drawings) to deliver electricity to the electrode 20, thereby activating tissues outside the OCT scanning probe 1a. The present disclosure is not limited to the electrical connection between the auxiliary localization component 40 and the electrode 20. In some embodiments, the auxiliary localization component 40 is nonconductive and insulated from the electrode 20, with additional conductive line provided to be electrically connected with the electrode 20.

When the light beam emitted from the optical fiber 320 passes through the light transmittable portion 110 of the tubular housing 10, since the auxiliary localization component 40 overlaps part of the light transmittable portion 110, some amount of light in the light beam interacts with the auxiliary localization component 40, thereby causing a characteristic in the aforementioned tomographic image, with the characteristic corresponding to the auxiliary localization component 40. Details about the interaction of auxiliary localization component and the characteristic in tomographic image will be described hereafter.

In this embodiment, the OCT scanning probe 1a further includes an indicating component 50 disposed on the outer surface of the tubular housing 10, and the indicating component 50 has a mark 510 at a direction corresponding to the auxiliary localization component 40. In detail, the indicating component 50 may be an annular block mounted on the outer surface of the tubular housing 10, and the mark 510 may be protrusion, recess, letter symbol, pattern or combination thereof. In an axial direction of the tubular housing 10, the auxiliary localization component 40 and the mark 510 are aligned, such that the orientation of the auxiliary localization component 40 can be determined by viewing the mark 510.

Figure 2:
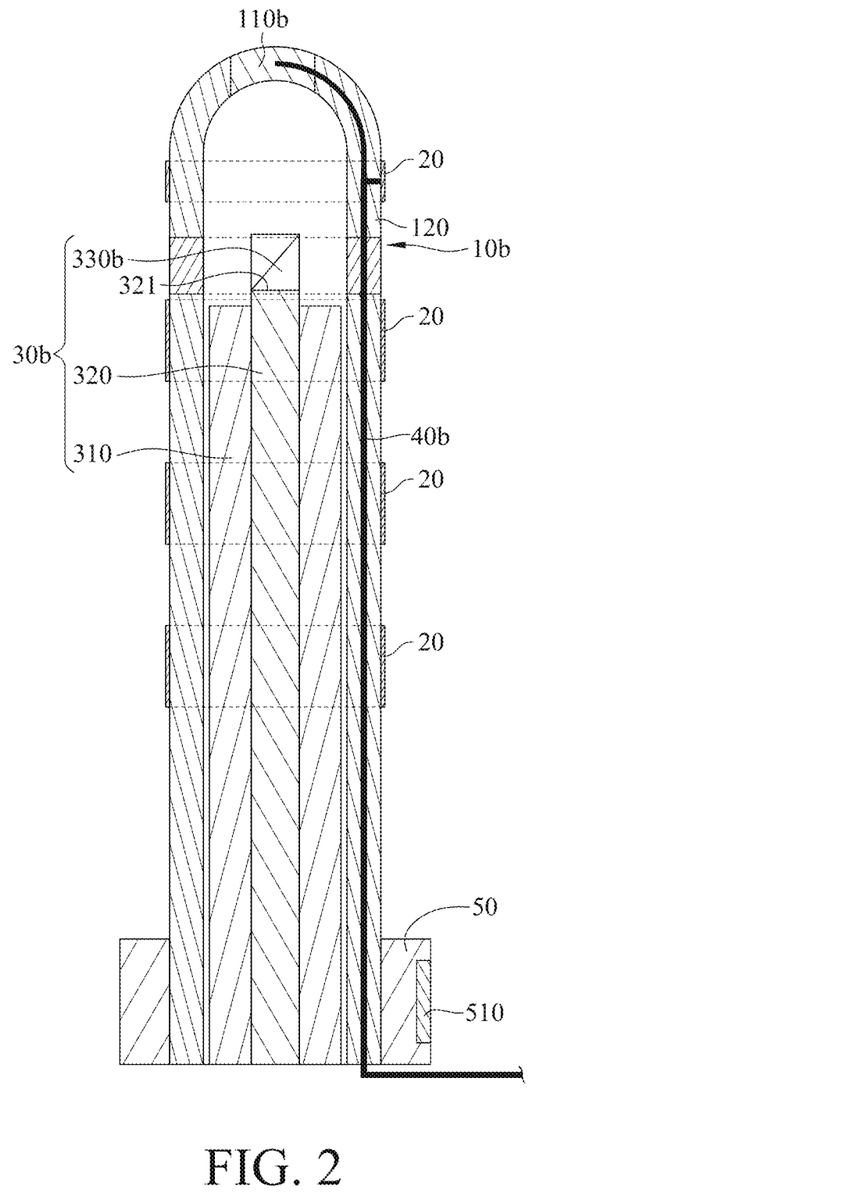
FIG. 2 is a schematic view of an OCT scanning probe according to a second embodiment of the present disclosure.

The present disclosure is not limited to the OCT scanning probe shown in FIG. 1. Please refer to FIG. 2 showing a schematic view of an OCT scanning probe according to a second embodiment of the present disclosure. In this embodiment, an OCT scanning probe 1b includes a tubular housing 10b, a plurality of electrodes 20, an optical fiber scanner 30b, an auxiliary localization component 40b and an indicating component 50. Regarding the electrode 20 and the indicating component 50 in FIG. 2, any detail can be referred to the foregoing description of corresponding component in FIG. 1, and any detail description about the electrode 20 and the indicating component 50 will be omitted hereafter.

The tubular housing 10b includes a light transmittable portion 110b and an opaque portion 120. In this embodiment, the light transmittable portion 110b of the tubular housing 100b is located on a closed end of the tubular housing 100b. The size of the light transmittable portion 110b depends on specifications of the optical fiber for scanning, and the present disclosure is not limited to the light transmittable portion 110b in the drawings. According to the location of the light transmittable portion 110b, the optical element 330b of the optical fiber scanner 30b may be a focusing lens configured to converge light beam emitted from the optical fiber 320, and the converged light beam reaches outside of the OCT scanning probe 1b through the light transmittable portion 110b. The auxiliary localization component 40b is disposed on the tubular housing 10b, and the auxiliary localization component 40b overlaps part of the light transmittable portion 110b. In one embodiment, auxiliary localization component 40b, for example, is a conductive line electrically connected with the electrodes 20, and extends to the closed end of the tubular housing 100b, thereby covering part of the light transmittable portion 110b. In other embodiments, the auxiliary localization component 40b may be a nonconductive line mark, and it covers part of the light transmittable portion 110b.

Figure 3:
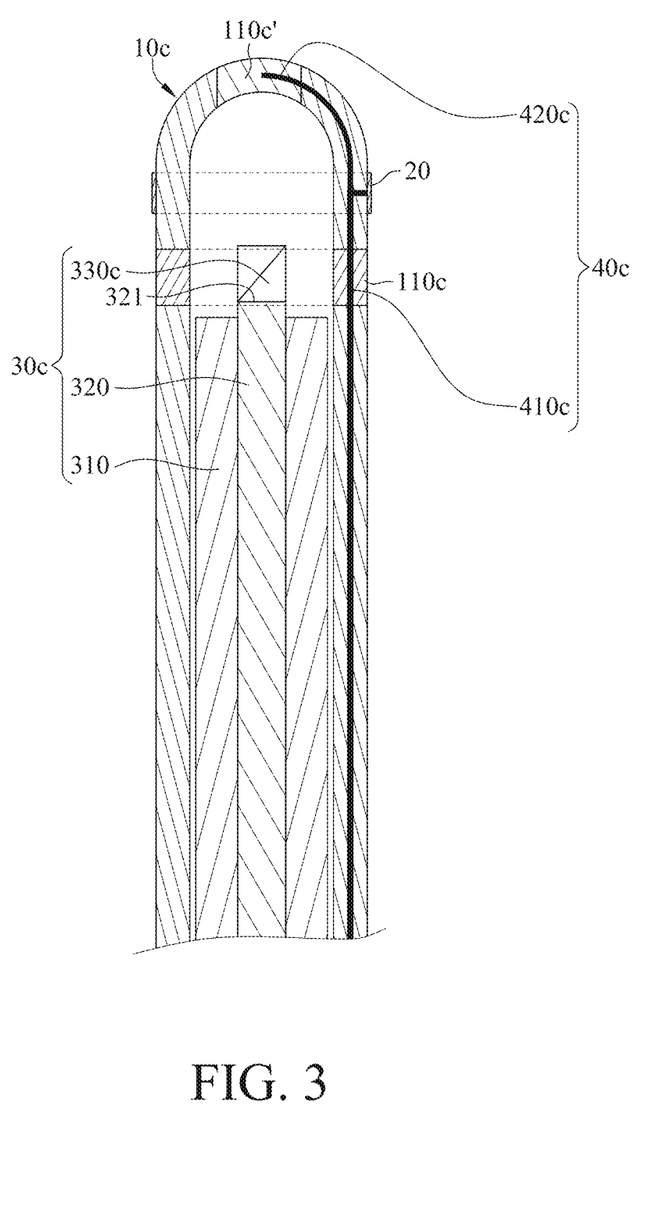
FIG. 3 is a schematic view of an OCT scanning probe according to a third embodiment of the present disclosure.

Please refer to FIG. 3 showing a schematic view of an OCT scanning probe according to a third embodiment of the present disclosure. In this embodiment, an OCT scanning probe 1c includes a tubular housing 10c, an electrode 20, an optical fiber scanner 30c and an auxiliary localization component 40c. Regarding the electrode 20 in FIG. 3, any detail can be referred to the foregoing description of corresponding component in FIG. 1, and any detail description about the electrode 20 will be omitted hereafter. For the purpose of illustration, an indicating component located on the outer surface of the tubular housing is omitted in FIG. 3.

The tubular housing 10c includes a first light transmittable portion 110c and a second light transmittable portion 110c'. The first light transmittable portion 110c is located on the side wall of the tubular housing 10c, and the second light transmittable portion 110c' is located on a closed end of the tubular housing 10c. With the first light transmittable portion 110c and the second light transmittable portion 110c' designated to be light transmittable, the rest of the tubular housing 10 may be light transmittable or opaque.

The optical fiber scanner 30c includes a base 310, an optical fiber 320 and an optical element 330c. The base 310 is rotatably disposed in the tubular housing 10c, and the optical fiber 320 is disposed on the base 310. The optical element 330c is disposed on the emitting end 321 of the optical fiber 320. To work with a configuration that the first light transmittable portion 110c and the second light transmittable portion 110c' are respectively at the side wall and the closed end of the tubular housing 10c, the optical element 330c may be a beam splitter in this embodiment. The optical element 330c corresponds to the first light transmittable portion 110c and the second light transmittable portion 110c'. The optical element 330c is configured to split the light beam emitted from the optical fiber 320 into a first sub-beam traveling toward the first light transmittable portion 110c and a second sub-beam traveling toward the second light transmittable portion 110c'. The two sub-beams pass through the first light transmittable portion 110c and the second light transmittable portion 110c', respectively, to reach outside of the OCT scanning probe 1c. The two sub-beams can illuminate different regions of a tissue outside the OCT scanning probe 1c, and an image sensor (not shown in the drawings) can receive the first and second sub-beams to obtain one or more tomographic images The auxiliary localization component 40c is disposed on the tubular housing 10c, and includes a first localization member 410c and a second localization member 420c. The first localization member 410c overlaps part of the first light transmittable portion 110c, and second localization member 420c overlaps part of the second light transmittable portion 110c'. In this embodiment, the first localization member 410c, for example, is a conductive line disposed in the side wall of the tubular housing 10c and electrically connected with the electrode 20. The first localization member 410c may be electrically connected with external power supply (not shown in the drawings) for supplying electricity to the electrode 20. The second localization member 420c is disposed on the closed end of the tubular housing 10c and electrically connected with the electrode 20. In some embodiments, each of the first localization member 410c and the second localization member 420c of the auxiliary localization component 40c may be a nonconductive line mark covering part of the first light transmittable portion 110c and part of the second light transmittable portion 110c', respectively.

When the light beam emitted from the optical fiber 320 passes through the first light transmittable portion 110c and the second light transmittable portion 110c', since the first localization member 410c overlaps part of the first light transmittable portion 110c and the second light transmittable portion 110c' overlaps part of the second localization member 420c, some amount of light in the light beam interacts with the auxiliary localization component 40c, thereby causing characteristics in a tomographic image, with one characteristic corresponding to the first localization member 410c and another characteristic corresponding to the second localization member 420c.

Figure 4:
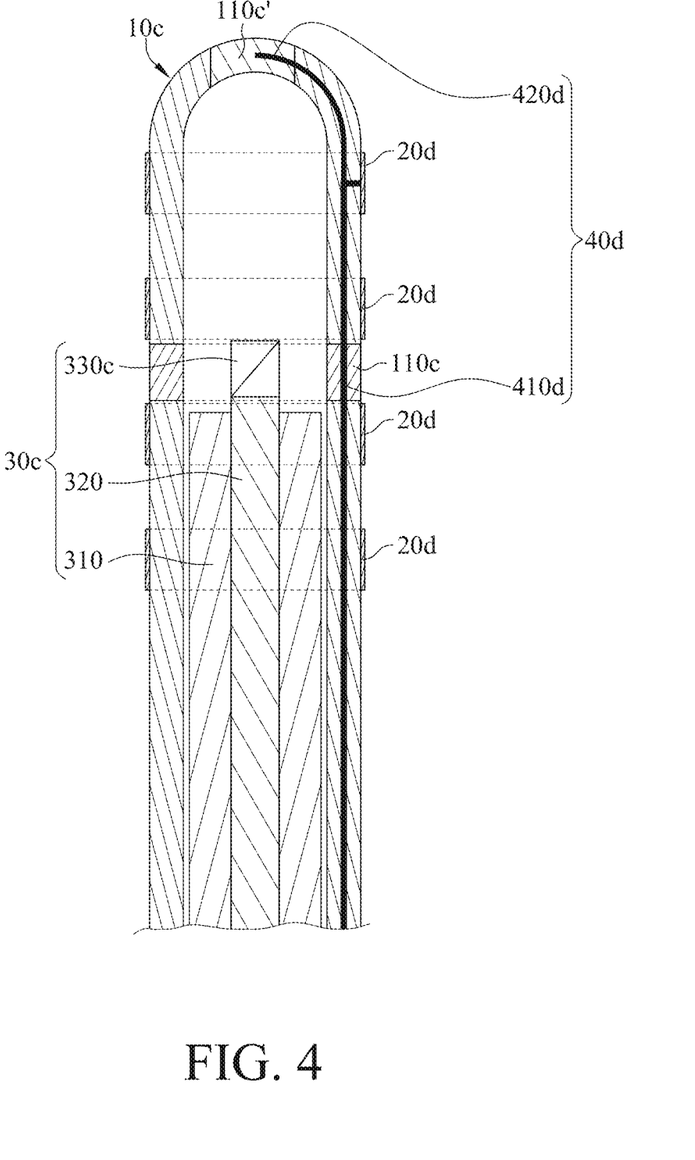
FIG. 4 is a schematic view of an OCT scanning probe according to a fourth embodiment of the present disclosure.

Please refer to FIG. 4 showing a schematic view of an OCT scanning probe according to a fourth embodiment of the present disclosure. In this embodiment, an OCT scanning probe 1d includes a tubular housing 10c, a plurality of electrodes 20d, an optical fiber scanner 30c and an auxiliary localization component 40d. Regarding the tubular housing 10c and the optical fiber scanner 30c in FIG. 4, any detail can be referred to the foregoing description of corresponding component in FIG. 3, and any detail description about the tubular housing 10c and the optical fiber scanner 30c will be omitted hereafter. For the purpose of illustration, an indicating component located on the outer surface of the tubular housing is omitted in FIG. 4.

Each of the electrodes 20d, for example, is an annular electrode ring disposed on the outer surface of the tubular housing 10c. The auxiliary localization component 40d includes a plurality of localization members which are at different positions of the tubular housing 10c. In detail, the auxiliary localization component 40d includes a plurality of first localization members 410d and a second localization member 420d. FIG. 4 exemplarily shows one of the first localization members 410d.

The first localization member 410d overlaps part of the first light transmittable portion 110c of the tubular housing 10c, and the second localization member 420d overlaps part of the second light transmittable portion 110c'. In this embodiment, each of the first localization members 410d, for example, is a conductive line disposed in the side wall of the tubular housing 10c and electrically connected with respective electrode 20d. The first localization member 410d can be electrically connected with external power supply (now shown in the drawings) to deliver electricity to the electrode 20d. The second localization member 420d is disposed on the closed end of the tubular housing 10c and electrically connected with the electrode 20d. It is noted that although there are multiple conductive lines electrically connected with the electrodes 20d, respectively, not every conductive line can be taken as the first localization member 410d or the second localization member 420d of the auxiliary localization component 40d. As to a conductive line which can be taken as a member of the auxiliary localization component 40d, it should at least cover part of the first light transmittable portion 110c and part of the second light transmittable portion 110c'. In some embodiments, both the first localization member 410d and the second localization member 420d of the auxiliary localization component 40d may be nonconductive line marks or printed patterns which cover part of the first light transmittable portion 110c and part of the second light transmittable portion 110c'.

Figure 5:
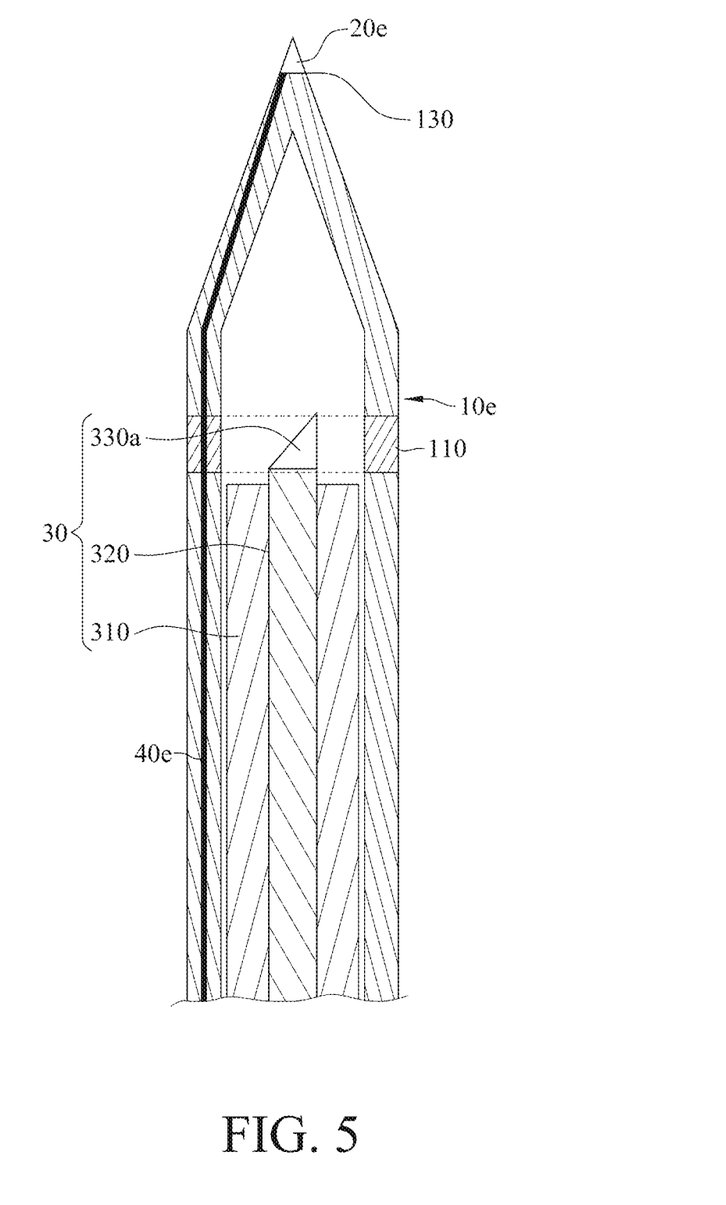
FIG. 5 is a schematic view of an OCT scanning probe according to a fifth embodiment of the present disclosure.

Please refer to FIG. 5 showing a schematic view of an OCT scanning probe according to a fifth embodiment of the present disclosure. In this embodiment, an OCT scanning probe 1e includes a tubular housing 10e, an electrode 20e, an optical fiber scanner 30 and an auxiliary localization component 40e. Regarding the optical fiber scanner 30 in FIG. 5, any detail can be referred to the foregoing description of corresponding component in FIG. 1, and any detail description about the optical fiber scanner 30 will be omitted hereafter. For the purpose of illustration, an indicating component located on the outer surface of the tubular housing is omitted in FIG. 5.

The tubular housing 10e, for example, is a transparent glass tube includes a light transmittable portion 110 on its side wall. Furthermore, the tubular housing 10e further includes a tapered end 130. The electrode 20e is disposed on the tapered end 130 of the tubular housing 10e, and the electrode 20e is located on the outer surface of the tubular housing 10e. In one embodiment, the tubular housing 10e and the electrode 20e can jointly work as a probe for measuring electrophysiological recordings of brain cells, and the electrode 20e substantially has the same size as human neuron.

The auxiliary localization component 40e is disposed on the tubular housing 10e, and the auxiliary localization component 40 overlaps part of the light transmittable portion 110. In this embodiment, the auxiliary localization component 40e, for example, is a conductive line disposed in the side wall of the tubular housing 10e and electrically connected with the electrode 20e. The auxiliary localization component 40e can be electrically connected with external power supply (now shown in the drawings) to deliver electricity to the electrode 20e.

Figure 6:
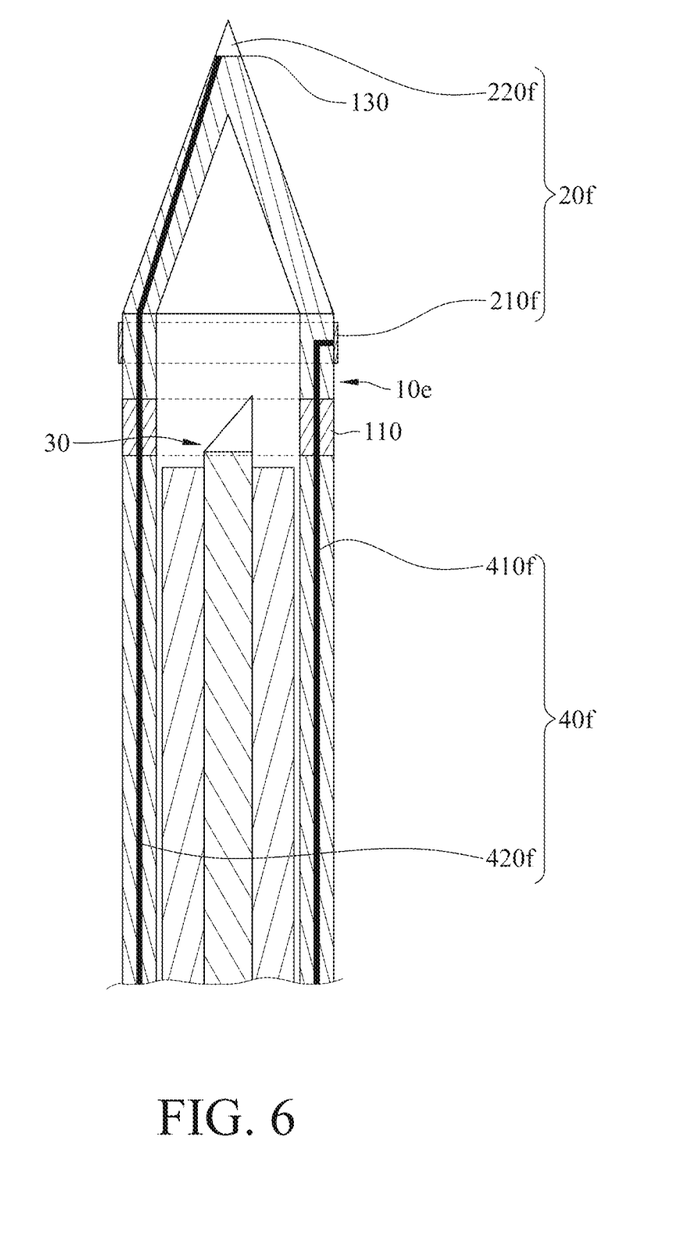
FIG. 6 is a schematic view of an OCT scanning probe according to a sixth embodiment of the present disclosure.

Please refer to FIG. 6 showing a schematic view of an OCT scanning probe according to a sixth embodiment of the present disclosure. In this embodiment, an OCT scanning probe if includes a tubular housing 10e, a plurality of electrodes 20f, an optical fiber scanner 30 and an auxiliary localization component 40f. Regarding the tubular housing 10e and the optical fiber scanner 30 in FIG. 6, any detail can be referred to the foregoing description of corresponding component in FIG. 1 and FIG. 5, and any detail description about the tubular housing 10e and the optical fiber scanner 30 will be omitted hereafter. For the purpose of illustration, an indicating component located on the outer surface of the tubular housing is omitted in FIG. 6.

The electrode 20f includes a first electrode 210f and a second electrode 220f. The first electrode 210f, for example, is an annular electrode ring disposed on the outer surface of the tubular housing 10e. The second electrode 220f is disposed on a tapered end 130 of the tubular housing 10e, and the second electrode 220f is disposed on disposed on the outer surface of the tubular housing 10e. The auxiliary localization component 40f is disposed on the tubular housing 10e, and the auxiliary localization component 40f includes a first localization member 410f and a second localization member 420f. The first localization member 410f and the second localization member 420f overlap parts of a light transmittable portion 110 of the tubular housing 10e. The first localization member 410f is disposed in the side wall of the tubular housing 10e and electrically connected with the first electrode 210f. The second localization member 420f is disposed in the side wall of the tubular housing 10e and electrically connected with the second electrode 220f. The first localization member 410f and the second localization member 420f can deliver electricity to the first electrode 210f and the second electrode 220f, respectively. In one embodiment, both the first localization member 410f and the second localization member 420f enclose an angle of 180 degrees with respect to an axis of the tubular housing 10e; in another embodiment, both the first localization member 410f and the second localization member 420f enclose an angle of 90 degrees with respect to the axis of the tubular housing 10e. The present disclosure is not limited to the aforementioned angle value between the localization member and the axis of the tubular housing.

Figure 7:
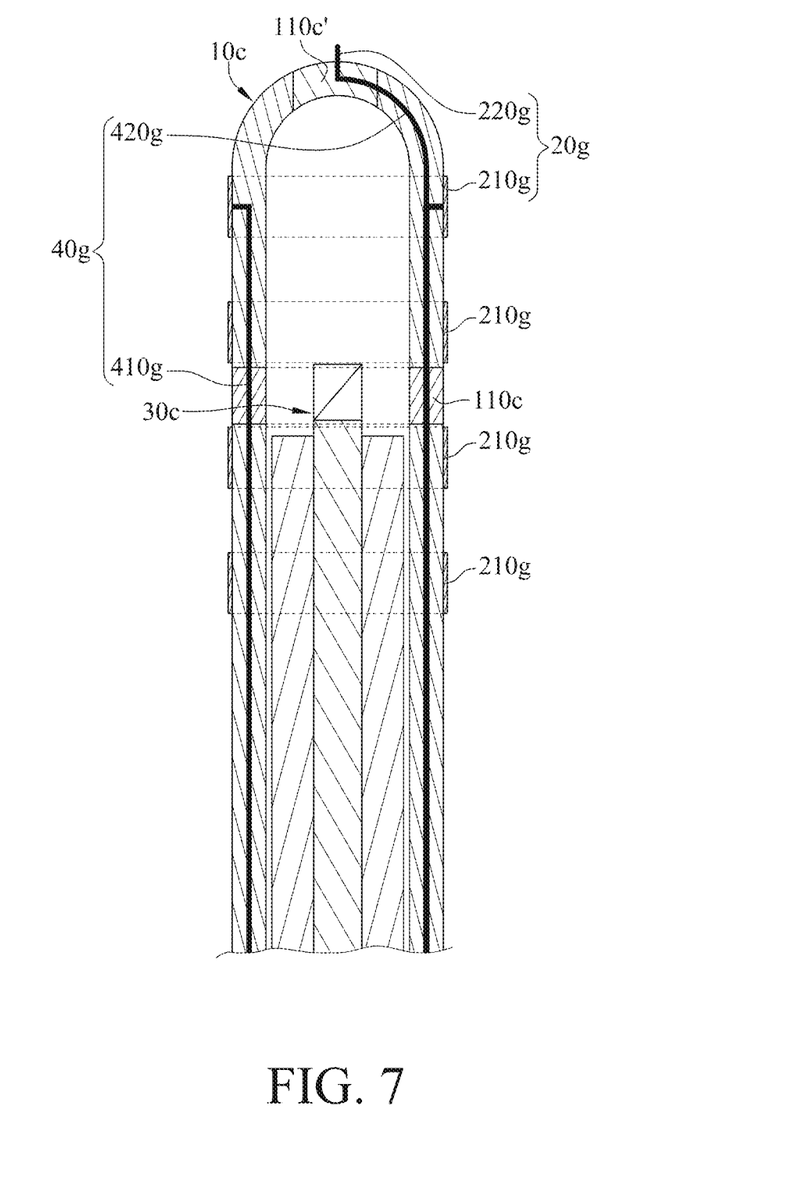
FIG. 7 is a schematic view of an OCT scanning probe according to a seventh embodiment of the present disclosure.

Please refer to FIG. 7 showing a schematic view of an OCT scanning probe according to a seventh embodiment of the present disclosure. An OCT scanning probe 1g includes a tubular housing 10c, a plurality of electrodes 20g, an optical fiber scanner 30c and an auxiliary localization component 40g. Regarding the tubular housing 10c and the optical fiber scanner 30c in FIG. 7, any detail can be referred to the foregoing description of corresponding component in FIG. 4, and any detail description about the tubular housing 10c and the optical fiber scanner 30c will be omitted hereafter. For the purpose of illustration, an indicating component located on the outer surface of the tubular housing is omitted in FIG. 7.

The electrodes 20g includes a plurality of first electrodes 210g and a second electrode 220g. Each of the first electrodes 210g, for example, is an electrode ring disposed on the outer surface of the tubular housing 10c. The first electrode 210g is identical to the electrode 20d in FIG. 4, and will not go into details hereafter. The second electrode 220g is disposed on a hemispherical closed end of the tubular housing 10c, and the second electrode 220g is located on the outer surface of the tubular housing 10c. In this embodiment, the second electrode 220g is a tip of the electrodes 20g extending outward from the outer surface of the tubular housing 10c, and the tip substantially has the same size as human neuron.

The auxiliary localization component 40g includes a plurality of first localization member 410g and a second localization member 420g. The first localization members 410g overlap part of the tubular housing 10c, and the second localization member 420g overlaps part of the tubular housing 10c. The first localization members 410g are disposed in the side wall of the tubular housing 10c, and the first localization members 410g are electrically connected with the first electrodes 210g, respectively. FIG. 7 exemplarily shows one of the first localization members 410g. The second localization member 420g is disposed in the side wall of the tubular housing 10c, and the second localization member 420g is electrically connected with the second electrode 220g. In one embodiment, both the first localization member 410g and the second localization member 420g enclose an angle of 180 degrees with respect to an axis of the tubular housing 10c; in another embodiment, both the first localization member 410g and the second localization member 420g enclose an angle of 90 degrees with respect to the axis of the tubular housing 10c. The present disclosure is not limited to the aforementioned angle value between the localization member and the axis of the tubular housing.

It is noted that although there are multiple conductive lines electrically connected with the electrodes 20g, respectively, not every conductive line can be taken as the auxiliary localization component 40g. As to a conductive line which can be taken as a member of the auxiliary localization component 40g, it should at least cover part of the first light transmittable portion 110c and part of the second light transmittable portion 110c'. In some embodiments, both the first localization member 410g and the second localization member 420g of the auxiliary localization component 40g may be nonconductive line marks or printed patterns which cover part of the first light transmittable portion 110c and part of the second light transmittable portion 110c'.

Figure 8:
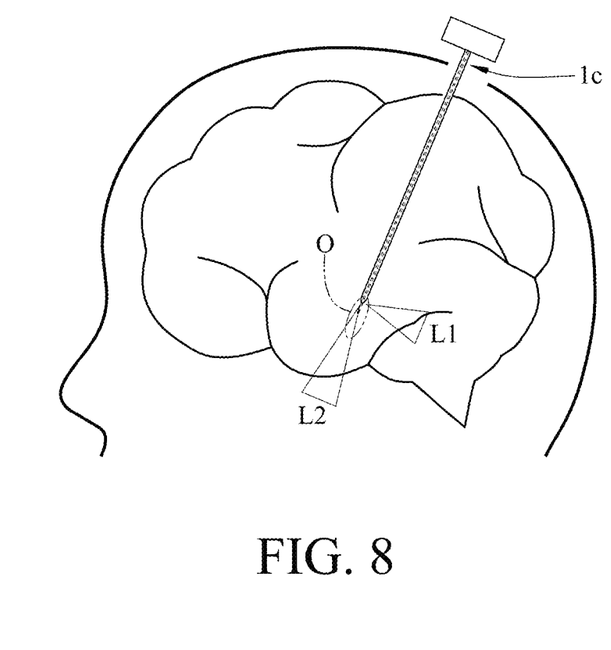
FIG. 8 is a schematic view showing location of a surgery target identifying by the OCT scanning probe in FIG. 3.

The following description is related to application of the OCT scanning probe in DBS. According to the present disclosure, the OCT scanning probe is applicable for identifying a surgical target in DBS target localization procedure. Please refer to FIG. 3 and FIG. 8, and FIG. 8 is a schematic view showing location of a surgery target identifying by the OCT scanning probe in FIG. 3. In FIG. 8, a target O may be a human STN.

The OCT scanning probe 1c is inserted into human brain, and electricity is supplied to the electrode 20 for measuring electrophysiological recordings. The optical fiber scanner 30c rotates, and the optical element 330c splits the light beam emitted from the optical fiber 320 into a first sub-beam L1 and a second sub-beam L2. The first sub-beam L1 passes through the first light transmittable portion 110c of the tubular housing 10c to obtain a first tomographic image. Since the first localization member 410c of the auxiliary localization component 40c has a larger size than or equal size to an optical resolution of the optical fiber 320 of the optical fiber scanner 30c, some amount of light in the first sub-beam L1 interacts with the first localization member 410c, thereby causing a first characteristic in the first tomographic image, with the first characteristic corresponding to the first localization member 410c. Similarly, the second sub-beam L2 passes through the second light transmittable portion 110c' of the tubular housing 10c to obtain a second tomographic image. Since the second localization member 420c of the auxiliary localization component 40c also has a larger size than or equal size to the optical resolution of the optical fiber 320, some amount of light in the second sub-beam L2 interacts with the second localization member 420c, thereby causing a second characteristic in the second tomographic image, with the second characteristic corresponding to the second localization member 420c. According to the electrophysiological recordings measured by the electrode 20 and the aforementioned tomographic images, a specific location of the OCT scanning probe 1c with respect to the target O (for example, at the middle, right side or left side of the human STN) can be accurately determined.

The following description is related to application of the OCT scanning probe in DBS electrode implantation procedure, and the present disclosure helps the implantation of DBS electrode at correct region. Please refer to FIG. 1 and FIG. 9, and FIG. 9 is a schematic view showing implantation of an electrode by the OCT scanning probe in FIG. 1

Figure 9:
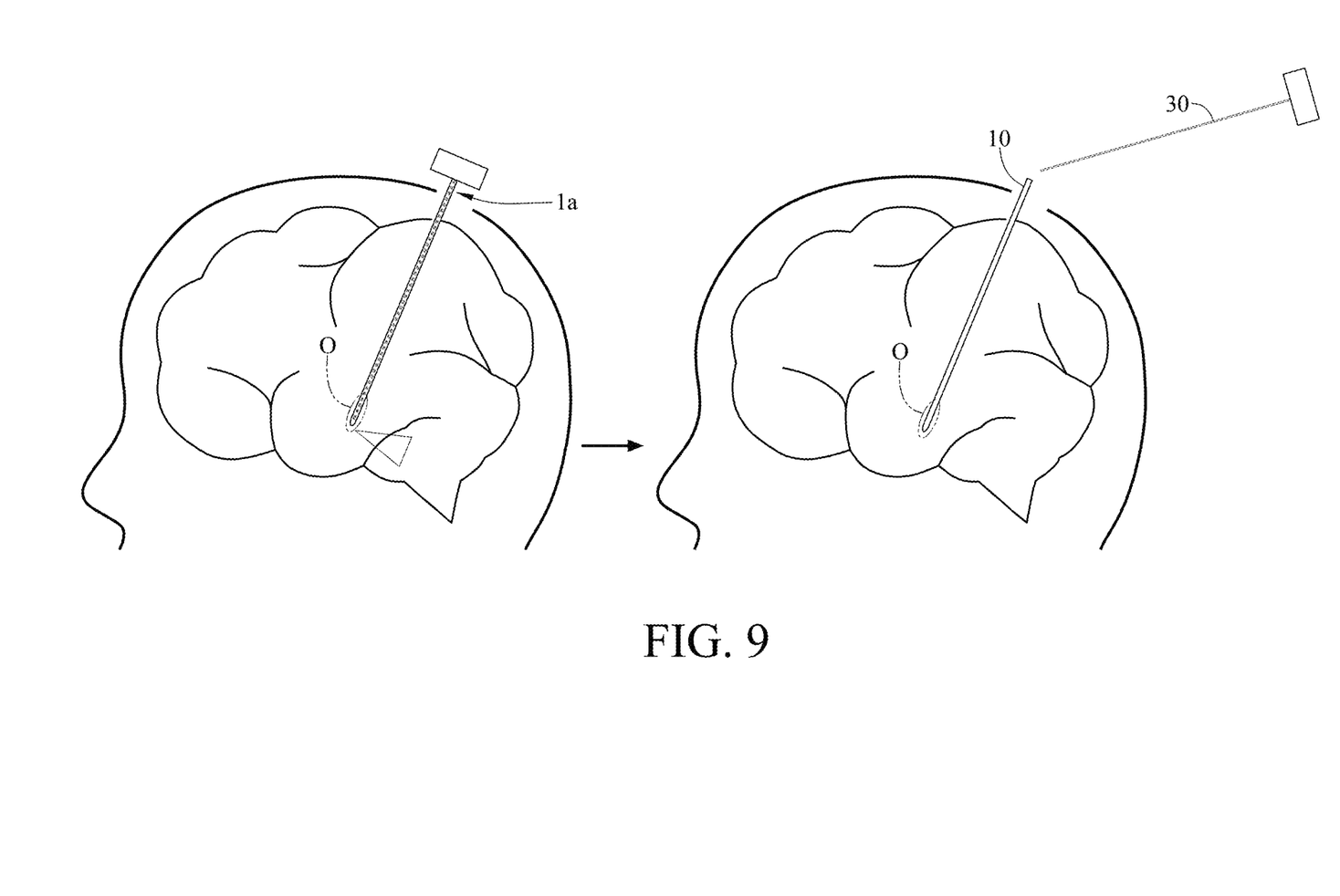
FIG. 9 is a schematic view showing implantation of an electrode by the OCT scanning probe in FIG. 1.

The OCT scanning probe 1a is inserted into human brain, and the optical fiber scanner 30 rotates with a light beam emitted from the optical fiber 320 (referring to FIG. 9). When the light beam passes through the light transmittable portion 110 of the tubular housing 10, since the auxiliary localization component 40 has a larger size than or equal size to the optical resolution of the optical fiber 320 of the optical fiber scanner 30, the light beam, which has interacted with the auxiliary localization component 40, generates a tomographic image, and the tomographic image contains a characteristic corresponding to the auxiliary localization component 40. According to the tomographic image mentioned above, the specific location of the OCT scanning probe 1a with respect to the target O can be accurately determined. Thus, it can be deduced that whether the electrode 20 of the OCT scanning probe 1a is at the central region of the target O. Once it is determined that the electrode 20 is at correct region, the optical fiber scanner 30 can be removed from the tubular housing 10. The residual elements in human brain, such as the tubular housing 10 and the electrode 20, work as a permanent DBS lead which can be turned on to effect the physiology of brain cells and neurotransmitters.

The aforementioned characteristic in the tomographic image varies with the properties of the auxiliary localization component. In one embodiment, the auxiliary localization component is made of opaque material, and some amount of light is blocked by the auxiliary localization component when the light beam passes through the light transmittable portion, and thus a dark zone corresponding to the auxiliary localization component is formed in the tomographic image. In another embodiment, the auxiliary localization component is made of metal material or includes metal coating, and some amount of light is reflected by the auxiliary localization component when the light beam passes through the light transmittable portion, and thus a bright zone corresponding to the auxiliary localization component is formed in the tomographic image. "The light beam interacts with the auxiliary localization component" or "the interaction of the light beam with the auxiliary localization component" means that the auxiliary localization component blocks light to cause dark zone, or the auxiliary localization component reflects light to cause bright zone.

Figure 10:
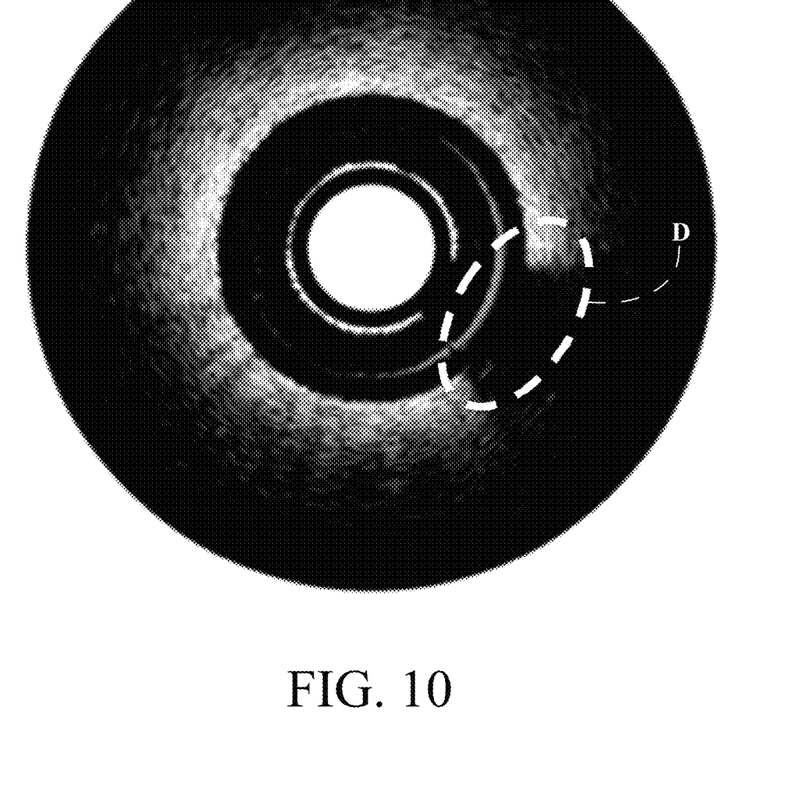
FIG. 10 is a tomographic image obtained by the OCT scanning probe in FIG. 9.

The following description is related to determining the location of the OCT scanning probe with respect to the target according to the tomographic image. FIG. 10 is a tomographic image obtained by the OCT scanning probe in FIG. 9. Some amount of light in the light beam passing through the light transmittable portion 110 of the tubular housing 10 is blocked by the auxiliary localization component 40, such that a dark zone D (characteristic) corresponding to the auxiliary localization component 40 is formed in the tomographic image of FIG. 10. According to the regions nearby the dark zone D in the tomographic image, it can be determined that whether the OCT scanning probe 1a is inserted into the target O; or, after the OCT scanning probe 1a is inserted into the target O, it can be determined that the OCT scanning probe 1a is currently at the central region of the target O or deviated from the central region, and thus one (person or device) can judge if the electrode should be re-implanted.

In some embodiments, since the OCT scanning probe for DBS is buried deep in the brain, it may be difficult for one (for example, a surgeon) to find the auxiliary localization component during DBS. For the purpose of convenient operation, an indicating component 50 can be selectively disposed on the tubular housing 10, and the indicating component 50 includes a mark 510 corresponding to the auxiliary localization component 40. Therefore, an orientation of the auxiliary localization component 40 can be determined by the mark 510.

According to the present disclosure, the OCT scanning probe includes an auxiliary localization component which overlaps a light transmittable portion. A light beam emitted from an optical fiber scanner is blocked or reflected by the auxiliary localization component when passing through the light transmittable portion, thereby causing a characteristic (dark zone or bright zone) in a tomographic image. The location of the OCT scanning probe with respect to a surgical target can be determined according to the characteristic. Thus, the OCT scanning probe helps to position the target or determine whether the electrode is at the central region of the target, thereby improving the effects to physiology of brain cells and neurotransmitters.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. An optical coherence tomography (OCT) scanning probe, comprising:
    a tubular housing;
    at least one electrode disposed on an outer surface of the tubular housing;
    an optical fiber scanner disposed in the tubular housing, wherein the optical fiber scanner comprising an optical fiber and an optical element, the optical element is disposed on an emitting end of the optical fiber, and the optical element is at corresponding position to a light transmittable portion of the tubular housing; and
    an auxiliary localization component disposed on the tubular housing, and the auxiliary localization component overlaps part of the light transmittable portion;
    wherein the light transmittable portion of the tubular housing comprises a first light transmittable portion and a second light transmittable portion, the first light transmittable portion is located on a side wall of the tubular housing, the second light transmittable portion is located on a closed end of the tubular housing, the optical element is a beam splitter, and the beam splitter corresponds to the first light transmittable portion and the second light transmittable portion;
    wherein the auxiliary localization component comprises a first localization member and a second localization member, the first localization member overlaps the first light transmittable portion, the second localization member overlaps the second light transmittable portion, the optical element splits a light beam emitted from the optical fiber scanner into a first sub-beam and a second sub-beam,
    the first sub-beam passes through the first light transmittable portion to obtain a first tomographic image, and an interaction of part of the first sub-beam with the first localization member causes a first characteristic in the first tomographic image, with the first characteristic corresponding to the first localization member,
    the second sub-beam passes through the second light transmittable portion to obtain a second tomographic image, and an interaction of part of the second sub-beam with the second localization member causes a second characteristic in the second tomographic image, with the second characteristic corresponding to the second localization member.

2. The OCT scanning probe according to claim 1, wherein the first characteristic is a dark zone in the first tomographic image, the second characteristic is a dark zone in the second tomographic image, the interaction of the first sub-beam with the first localization member is that the first localization member blocks the first sub-beam, and the interaction of the second sub-beam with the second localization member is that the second localization member blocks the second sub-beam.

3. The OCT scanning probe according to claim 1, wherein the first characteristic is a bright zone in the first tomographic image, the second characteristic is a bright zone in the second tomographic image, the interaction of the first sub-beam with the first localization member is that the first localization member reflects the first sub-beam, and the interaction of the second sub-beam with the second localization member is that the second localization member reflects the second sub-beam.

4. The OCT scanning probe according to claim 1, wherein the optical fiber scanner further comprises a base, the optical fiber is disposed on the base, the base is rotatably disposed in the tubular housing and brings the optical fiber to rotate together.

5. The OCT scanning probe according to claim 1, wherein the optical fiber scanner further comprises a base, the optical fiber is disposed in the base and rotatable relative to the base.

6. The OCT scanning probe according to claim 1, wherein each of the first localization member and the second localization member of the auxiliary localization component is a conductive line electrically connected with the at least one electrode.

7. The OCT scanning probe according to claim 1, wherein the at least one electrode comprises an electrode ring disposed on the outer surface of the tubular housing.

8. The OCT scanning probe according to claim 1, wherein the at least one electrode is disposed on a hemispherical closed end of the tubular housing, and the at least one electrode is a tip extending outward from the outer surface of the tubular housing.

9. The OCT scanning probe according to claim 1, further comprising an indicating component disposed on the outer surface of the tubular housing, wherein the indicating component has a mark at a direction corresponding to one of the first localization member and the second localization member of the auxiliary localization component.

10. The OCT scanning probe according to claim 1, wherein a size of each of the first localization member and the second localization member of the auxiliary localization component is larger than or equal to an optical resolution of the optical fiber scanner.

11. The OCT scanning probe according to claim 1, wherein the first localization member and the second localization member of the auxiliary localization component is located in the side wall of the tubular housing.

12. The OCT scanning probe according to claim 11, wherein the tubular housing has a tapered end, and the at least one electrode is disposed on the tapered end.

13. The OCT scanning probe according to claim 1, wherein the optical fiber scanner is detachably disposed in the tubular housing.

* * * * *